(12) United States Patent
Schuhbauer et al.

(10) Patent No.: US 7,993,676 B2
(45) Date of Patent: Aug. 9, 2011

(54) FREE-FLOWING, POWDERY COMPOSITION CONTAINING ALPHA-LIPONIC ACID (DERIVATES)

(75) Inventors: Hans Schuhbauer, Edmonton (CA); Claus-Peter Drexel, Neu-Isenburg (DE); Herbert Clinton Fairow, Tolono, IL (US); Hans-Peter Krimmer, Kirdweidach (DE)

(73) Assignee: Alzchem Trostberg GmbH, Trostberg (DE)

( * ) Notice: Subject to any disclaimer, the term of this patent is extended or adjusted under 35 U.S.C. 154(b) by 786 days.

(21) Appl. No.: 10/515,671

(22) PCT Filed: May 28, 2003

(86) PCT No.: PCT/EP03/05663
§ 371 (c)(1), (2), (4) Date: Apr. 21, 2005

(87) PCT Pub. No.: WO03/099256
PCT Pub. Date: Dec. 4, 2003

(65) Prior Publication Data
US 2005/0220884 A1  Oct. 6, 2005

(30) Foreign Application Priority Data
May 29, 2002 (DE) .................................. 102 23 882

(51) Int. Cl.
*A61K 9/14* (2006.01)
*A61K 31/385* (2006.01)
*A01N 43/26* (2006.01)

(52) U.S. Cl. ........................................ 424/489; 514/440
(58) Field of Classification Search .................. 424/489; 514/440
See application file for complete search history.

(56) References Cited

U.S. PATENT DOCUMENTS

| | | | |
|---|---|---|---|
| 2,871,154 A * | 1/1959 | Searle et al. ................... | 514/440 |
| 4,623,478 A * | 11/1986 | Pastorino ....................... | 516/11 |
| 4,775,540 A | 10/1988 | Hertel et al. | |
| 5,455,264 A * | 10/1995 | Beisswenger et al. ........ | 514/440 |
| 5,691,294 A * | 11/1997 | France et al. .................. | 510/349 |
| 6,271,254 B1 * | 8/2001 | Ulrich et al. ................... | 514/440 |
| 6,902,715 B2 * | 6/2005 | Maus et al. ..................... | 423/335 |
| 2001/0039292 A1 * | 11/2001 | Packer et al. .................. | 514/440 |

FOREIGN PATENT DOCUMENTS

| | | |
|---|---|---|
| DE | 42 18 768 A1 | 12/1993 |
| DE | 199 38 098 A | 2/2001 |
| EP | 0 427 247 B1 | 5/1991 |
| EP | 0 158 120 | 6/1992 |
| EP | 0 572 922 A1 | 12/1993 |
| EP | 0 858 802 A | 8/1998 |
| EP | 1290997 A1 * | 3/2003 |
| JP | 03-169813 | 7/1991 |
| JP | 06-135832 | 5/1994 |

OTHER PUBLICATIONS

Evonik Industries—Product Database sheet—Description of Aerosil 200, pp. 1-2.*
Degussa of Evonik Industries—Product Information Sipernat 22. Description of Sipemat 22. pp. 1-3.*
NIOSH-CDC Pocket Guide to Chemical Hazards, Sep. 2000, pp. 1-2.*
Harwick Standard Data Sheet. PPG Hi Sil 233 amorphous silicon dioxide, Apr. 2000, pp. 1-2.*
PPG Hi-Sil Data Sheet, Carrier Application Property Chart, p. 1.*
Evonik Industry. Aerosil 972 Data sheet, pp. 1-3.*
Degussa of Evonik Industries—Product Information Sipernat 22. Description of Sipernat, 2007, pp. 1-3.*
PPG Hi-Sil Data Sheet, Carrier Application Property Chart, 2008, p. 1.*
Evonik Industry. Aerosil 972 Data Sheet, 2008, pp. 1-3.*
"Free-flowing DBNPA compositions", *Chem. Abstr.* 60438c, 132(6), (2000), p. 239.
List et al. "Hagers Handbuch der Pharmazeutischen Praxis", vol. 7b, Hilfsstoffe, 4th Ed. (1977), pp. 258-261.
Degussa AG, Business Line Silicas and Silanes—product information—Sipernat 50S (2002).
Degussa AG, Business Line Silicas and Silanes—product information—Sipernat 22S (2002).
Pharmazeutischen Praxis, Springer-Verlag (1977) (*excerpts*) with English translation.

* cited by examiner

*Primary Examiner* — Sreeni Padmanabhan
*Assistant Examiner* — Samira Jean-Louis
(74) *Attorney, Agent, or Firm* — Fulbright & Jaworski L.L.P.

(57) ABSTRACT

A free-flowing, powdery composition contains a lipoic acid component and from 0.1 to 25% by weight of the total composition of a silica-based flow aid having a particle size (×100 value) of <800 μm.

19 Claims, No Drawings

FREE-FLOWING, POWDERY COMPOSITION CONTAINING ALPHA-LIPONIC ACID (DERIVATES)

This is a §371 from PCT/EP03/05663 filed May 28, 2003 which claims priority from German 102 23 882.0 filed May 29, 2002.

The present invention relates to a free-flowing, powdery composition containing α-lipoic acid (derivatives), to a process for the production thereof and to the use thereof.

α-Lipoic acid (thioctic acid, 1,2-dithiolane-3-pentanoic acid) has been known for about 50 years as a growth factor in microorganisms, but it also occurs as the R-(+) enantiomer in low concentrations in higher plants and animals. The physiological action of α-lipoic acid in hydrophilic and lipophilic media is as a coenzyme of the oxidative decarboxylation of α-keto carboxylic acids (e.g. pyruvate, α-ketoglutarate). In addition, α-lipoic acid is also involved as cofactor in the degradation of certain amino acids. It moreover contributes to the regeneration of vitamin C, vitamin E, glutathione and coenzyme Q10. Further, α-lipoic acid and its relevant redox partner dihydrolipoic acid have strongly antioxidant and occasionally also prooxidant properties; α-lipoic acid is therefore often referred to as "universal antioxidant". Racemic α-lipoic acid is employed both as pure solid mixed with other components, in solid pharmaceutical formulations, but also in infusion solutions, as active pharmaceutical ingredient or as addition to food. Racemic α-lipoic acid is approved for the treatment of liver disorders and neuropathies (e.g. diabetic polyneuropathy); its use as an efficient inhibitor of the replication of HIV-1 viruses has been suggested (cf. *Klin. Wochenschr.* 1991, 69(15), 722-724). Injection solutions of α-lipoic acid are preferably employed chiefly in the initial stage of corresponding clinical therapy. The R enantiomer of α-lipoic acid has been in clinical phase II for applications in the area of type II diabetes in Germany since Dec. 2000 and in the USA since May 2001.

Methods for synthesizing racemic α-lipoic acid and for enantiopure R- or S-α-lipoic acid are described or summarized for example in Crévisy et al., Eur. J. Org. Chem. 1998, 1949, Fadnavis et al., Tetrahedron Asym. 1998, 9, 4109, Dhar et al., J. Org. Chem. 1992, 57, 1699, Adger et al., J. Chem. Soc. Chem. Commun. 1995, 1563, Dasaradhi et al., J. Chem. Soc. Chem. Commun. 1990, 729, Gopalan et al., J. Chem. Soc. Perkin Trans. I 1990, 1897, Yadav et al., J. Sci,. Ind. Res. 1990, 49, 400, Tolstikov et al., Bioorg. Khim. 1990, 16, 1670, Gopalan et al., Tetrahedron Lett. 1989, 5705.

Compounds with a low solidification point, like the 60-62° C. of racemic α-lipoic acid or 47-50° C. of enantiopure R-(+)- or S-(−)-α-lipoic acid, form, at temperatures in the vicinity of their melting point, soft surfaces which result in adhesion of individual particles to one another. The sensitivity of racemic or enantiopure α-lipoic acid to the effects of light and temperature, and a general tendency to polymerizability additionally have adverse effects. The reason for this sensitivity is that the characteristic disulfide bond in the strained five-membered ring in the lipophilic chain of the molecule can be cleaved extremely easily. Such a cleavage is associated with an intermolecular formation of disulfide bridges, which leads to dimeric, oligmeric and polymeric lipoic acid derivatives (cf. DE 1617740). This may take place through the effect of light or temperature, but also through the presence of nucleophiles (*J. Org. Chem.* 1969, 34, 3131). Oxidative decomposition is also disclosed in the literature (*J. Org. Chem.* 1975, 40, 58-62). This tendency to polymerization is even more pronounced for the pure enantiomers of α-lipoic acid than for the racemate. Because of the macroscopic properties of these lipoic acid polymers, the product has a general tendency to form adhesions and lumps. Moreover, a higher content of these polymers means a greater tendency to lumps and a more pronounced reduction in the flowability of the product.

The usual method used for purifying crude α-lipoic acid is recrystallization from organic solvents such as, for example, n-pentane, cyclohexane, methylcyclohexane, ethyl acetate, or mixtures of solvents (e.g. of ethyl acetate and hexane), as described for example in Brookes et al., J. Chem. Soc. Perkin Trans. 1 1988, 9, Segre et al., J. Am. Chem. Soc. 1957, 3503, Walton et al., J. Am. Chem. Soc. 1955, 77, 5144, Acker et al., J. Am. Chem. Soc. 1954, 76, 6483.

Also implemented industrially are processes for the extraction and/or crystallization of α-lipoic acid, which provide for the use of organic solvents having a dielectric constant ∈ of from 2.5 to 5.5 (DE 42 35 912) or 1.95 to 2.4 (EP 1 100 793).

Working up the mother liquors to increase the yield and thus the efficiency of the process is technically very complicated and generally leads to a deterioration in the flowability and to an increase in the tendency to lumps. DE 197 26 519 A1 proposes, as alternative additional method for purifying lipoic acid which has previously been recrystallized from a mixture of cyclohexane and ethyl acetate, a treatment of the crude material enriched with lipoic acid with liquid or supercritical carbon dioxide. According to DE 199 38 621, dissolving crude α-lipoic acid in dilute aqueous alkaline solution, removal of solid impurities present by filtration and reacidification results in a crystalline α-lipoic acid which is distinguished by the absence of impurities such as 1,2,3-trithiane-4-valeric acid (epilipoic acid) and the absence of organic solvents.

EP-A 733 363 describes an agglomerated granulate of α-lipoic acid which is obtained by means of an elaborate process after introducing α-lipoic acid into a fluidized bed device by spraying an α-lipoic acid solution onto the introduced material while simultaneously removing the solvent. Such an α-lipoic acid has a specific surface area of >0.7 m$^2$/g and a proportion of mesopores with a diameter between 2 and 30 nm. This high specific surface area leads, in conjunction with different particle sizes, frequently to demixing, with the larger particles moving faster than the small ones, especially during transport, during transfer or conveying. The shape of the particles of this agglomerated granulate also impairs the flowability of the product, because an irregular surface leads to increased friction and to more ensnarement of the particles by one another. In addition, the residual solvent content in such agglomerated granulate results in increased particle adhesion in the product which is mediated by capillary fluids in the partly or completely filled mesopore space.

The processes known in the prior art make it possible, despite a considerable increase in technical complexity and with yields which are unfavorable for commercial production of α-lipoic acid, for the flowability of the product to be improved to only a very limited extent and moreover insufficiently for many industrial applications. The α-lipoic acid qualities obtainable to date are thus in a form which is unfavorable even just for further processing to solid dosage forms. It is also a well-known fact that in the production of solid dosage forms of α-lipoic acid even apparently well-tried formulas sometimes give inexplicable results with α-lipoic acid batches differing in provenance, even if all the process procedures are complied with, usually being manifested by insufficient qualities of product. In addition, although it is certainly acknowledged that, for example, the particle size distribution of the α-lipoic acid batch employed represents an important characteristic for tabletability, it has not yet been possible to specify the key parameters appropriately. If not all the important binding mechanisms (sintered bridges, crystallization and structural modifications, liquid bridges, chemical bonds, adhesion through capillary fluids) are known, it is usually impossible to prevent particle agglomerations.

The addition of various types of flow aids is widespread in pharmaceutical technology for active ingredients of solid dosage forms in order to reduce the adhesive forces between particles which are caused by particle adhesion, electrostatic adhesion, van der Waals forces or liquid bridges. Examples of such flow aids in the form of synthetic silicas which are suitable for preventing sintering processes are Aerosil® 200 or Aerosil® 380 (both synthetic, highly dispersed silicas produced by the high-temperature hydrolysis process by Degussa AG) (*Pharm. Ind.* 1970, 32, 478). However, it was not possible to predict whether use of flow aids in combination with α-lipoic acid leads to improved qualities of product, or which specifications suitable flow aids ought to have.

The object of the present invention was thus to provide a composition containing α-lipoic acid (derivatives) which if possible shows no tendencies to agglomeration and which is not prone to clumping and adhere either. In addition, it was intended that the composition be processed further easily and without great efforts to solid dosage forms for pharmaceutical, dietetic or cosmetic purposes.

This object has been achieved with the aid of a free-flowing, powdery composition which comprises a lipoic acid component and from 0.1 to 25% by weight, based on the total weight of the composition, of a silica-based flow aid which has a particle size (×100 value) of <800 μm and a tamped density of from 50 to 600 g/l.

In this connection, the "×100 value" means, in contrast to the d50 value, that 100% of the particles employed have maximally the size stated in each case.

The claimed composition has distinctly improved properties in terms of flowability, flow behavior, sintering tendency and piling stability and its handling as solid during transfer or conveying is facilitated. This was not thus to be expected.

The composition is particularly distinguished by a markedly improved flowability compared with prior art qualities and additionally by a significantly improved flow behavior. This is because, surprisingly, the so-called "core flow" is almost completely suppressed in the composition of the invention through the use of specific flow aids in contrast to other flow aids. Thus, virtually the whole amount of powder moves during transfer, pouring or emptying, and the unwanted formation of "dead zones" is nearly completely suppressed.

Racemic α-lipoic acid and dihydrolipoic acid, enantiopure R-(+)- or S-(−)-α-lipoic acid and -dihydrolipoic acid or any mixtures thereof are to be regarded as preferred lipoic acid components. In addition, α-lipoic acid or else its natural lipoic acid redox partner dihydrolipoic acid may be wholly or partly in the form of their salts. Suitable salts in this connection are, in particular, the sodium, potassium, ammonium, magnesium or creatine lipoate and/or the sodium, potassium, magnesium or creatine dihydrolipoate. It is additionally possible for the lipoic acid and/or dihydrolipoic acid to be wholly or partly in the form of a salt with basic amino acids such as, for example, lysine, arginine or ornithine.

As described, it was possible to achieve the object on which this invention is based through the addition of certain flow aids to α-lipoic acid. Flow aids which have proved to be particularly suitable in this connection for achieving the desired improvements in quality and handling of α-lipoic acid are hydrophilic spray-dried precipitated silicas such as, for example, Sipernat® 22 S, Sipernat® 50 S and Sipernat® 500 LS (Degussa AG), or hydrophilic highly dispersed silicas such as, for example, of the Aerosil® 200 type, and hydrophobic silicas such as, for example, of the Aerosil® R972 type. The hydrophilic precipitated silicas of the Sipernat® 22 S, Sipernat® 50 S and Sipernat® 500 LS type moreover comply with the requirements for the food additive E 551 of the EU directive 2000/63/EU and are thus authorized for example for use in dry food products in powder form (including types of sugar) up to a maximum quantity of 10 g/kg and for powdered flavorings up to a maximum quantity of 1000 mg/kg. Flow aids which have likewise proved suitable for the purposes of the present invention are amorphous silica gels like those represented for example by the Sylox 2, 15 & T450 type (GRACE Davison, Columbia).

The proportion of flow aid component in the composition of the invention should be between 0.1 and 25% by weight based on the total weight of the product of the invention. Preferred proportions by weight of the flow aid are to be regarded as ranges between 1.0 and 10.0% by weight and particularly preferably those between 1.5 and 5.0% by weight. Ranges of 2.0-3.0% by weight are most preferred. All the proportions by weight stated here in relation to the flow aid are based on racemic or optically pure α-lipoic acid. This means that on use of lipoic acid derivatives or salts the stated dosage quantities correspond to those for free lipoic acid, for which reason they must be adjusted for the changed molecular weight.

The proportion of active ingredient component in the composition of the invention is preferably 50-99.9% by weight. A proportion of active ingredient component of 75-99.0% by weight is particularly preferred, and a proportion of 90.0-98.0% by weight is most preferred.

The hydrophilic or hydrophobic flow aids normally have excellent intrinsic flowability and can be adjusted by grinding specifically in relation to their features, essential to the invention, of particle size and tamped density.

In this connection, particle sizes (×100 value) which have proved to be particularly suitable in relation to the flow aid are <600 μm and in particular between 50 and 400 μm. Preferred ranges which have emerged in relation to the tamped density parameter are from 75 to 100 g/l, and it should be noted that these data relate to non-sieved flow aids.

For particular applications the specific surface area of the flow aid may also be important, which is why the present invention regards ranges between 30 and 1000 $m^2/g$ and in particular those between 190 and 450 $m^2/g$ as preferred. The specific surface areas were in this connection determined with an Areameter using nitrogen.

The pH which the flow aids employed in each case attain in aqueous solution may likewise be important. In this connection, the present invention has preference for flow aids which yield a pH of from 3.0 to 11.5 and in particular of from 6.0 to 7.0 in a concentration of 5% in aqueous solution.

A further advantage of the composition of the invention is to be regarded as being the fact that the lipoic acid component employed may be of any origin, i.e. the flowability is improved regardless of the synthesis route used for the preparation. The solvent and polymer content of the lipoic acid component is also immaterial within the scope of the usual specifications. Also suitable for the composition of the present invention are solvent-free α-lipoic acids like those described in DE 199 38 621 A, or prepared as described in DE 197 26 519 A1, DE 42 35 912 A, DE 198 34 608 A1, EP 586 987, DE 198 45 517 A1, EP 733 363 or EP 593 896, or purified racemic or enantiopure α-lipoic acids.

Besides the described composition, the present invention also claims a process for the production thereof, in which (a) the powdered lipoic acid component is mixed with the solid flow aid, and then (b) particles of >800 μm are removed from the resulting solid mixture.

It is moreover possible for the purposes of the present invention to repeat process steps (a) and/or (b) as often as desired.

The lack of complexity and the directness of the present process also represent considerable advantages of the present invention. Smaller amounts of the composition of the invention can be produced in a simple manner by mixing in a Turbula mixer for 3 minutes and then sieving. For industrial batches, mixing implements with low shear forces are to be preferred in process step (a), as are represented by free-fall mixers in the form of drum, V and tumbler mixers, horizontally operating paddle and plowshare mixers (e.g. Lödige mixers), vertically operating conical mixers, especially with flat-cut screws of the Nauta type, or Eirich mixers with diagonal mixing implements; also suitable are mixers with rapidly rotating mixing implements, mixers with pulsating air and screw or double screw mixers. Short mixing times of from 5 to 30 min duration and in particular 10 to 15minutes, and maximally fine distribution of the α-lipoic acid may overall be advantageous. It may therefore also be advisable to introduce the lipoic acid component by spraying a solution of the lipoic acid component onto a carrier silica with simultaneous removal of the solvent. Alternatively, metering in of the flow aid in a spray tower is also a particularly preferred embodiment of the present invention.

This is because moreover the sequence of addition of the flow aid and of the lipoic acid component is immaterial for the present process. However, the present invention preferably provides for addition in process stage (a) of at least one of the two components in portions. However, the components can be overall added in any frequency and proportions and at any speed.

It is thus possible with the aid of a simple process to mix the lipoic acid component rapidly and efficiently with the hydrophilic or hydrophobic flow aid component with exposure to low shear forces.

A lipoic acid-containing composition produced in this way inter alia can easily be processed further to appropriate dosage forms, for which the present invention provides the use in solid dosage forms for pharmaceutical, dietetic and/or cosmetic applications. It is possible in particular to produce, in a simplified manner, compressed administration forms and particularly preferably tablets with a high active ingredient content for oral applications, as are employed for example within the framework of a clinical therapy of diabetic polyneuropathy or type 2 diabetes.

In addition, the invention also includes the use of the composition for producing solutions for infusion.

Compared with lipoic acid-containing compositions disclosed to date in the prior art, the composition of the invention displays generally improved properties in relation to flowability, flow behavior, sintering tendency and piling stability. In addition, the handling as solid during transfer, pouring and/or conveying is significantly facilitated, which is why the present invention represents a considerable improvement of the lipoic-containing compositions disclosed to date.

These advantages of the free-flowing, powdery composition containing α-lipoic acid (derivatives) are to be illustrated by the following examples.

EXAMPLES

The following methods were employed to assess the properties of the product.

(a) Flowability Through Orifice Apparatuses.

The flowability without pressure treatment was determined by using siliconized glass orifice vessels with different orifice diameters (*Seifen, Öle, Fette, Wachse* 1968, 94, 12). The assessment took place in accordance with (rating) scores: 1=very good flow behavior (the powder to be investigated flows continuously out of orifice apparatus No. 1 with the smallest orifice) to score 6=inadequate flow behavior (the powder does not even flow out of measurement vessel No. 5 with the largest orifice). The measurement method was carried out always with the same sequence of orifice vessels 1 to 6. The measurement vessel with which the powdery composition just flows continuously out was determined (table 1).

TABLE 1

Assessment of the flowability with glass orifice vessels

| Vessel No. | Orifice width Ø [mm] | Assessment when the powder flows through just continuously |
|---|---|---|
| 1 | 2.5 | very good |
| 2 | 5 | good |
| 3 | 8 | quite good |
| 4 | 12 | just adequate |
| 5 | 18 | deficient |
| 6 |  | inadequate (powder does not flow through No. 5) |

(h = 80 mm, Ø (internal) = 38 mm)

(b) Flowability Through Height of Conical Heap

A metal sieve was fastened at a distance of 30-100 mm above a solid metal cylinder with a diameter of 50 mm and a height of about 80 mm. The distance between metal sieve and metal cylinder depended on the flowability of the powder to be measured and was somewhat larger than the height of the conical heap of the powder with the worst flow in the particular test series. The sieve was fixed at this height, and the powder was poured onto the sieve and slowly passed through it manually with the aid of a spatula. The descending powder thus forms a conical heap on the metal cylinder. The powder was then passed through the sieve until a cone with geometrically regular shape had formed on the cylinder. The sieve was then removed, and the height of the conical heap was measured. The angle of repose of the tested powder can be determined from the height of the conical heap and the diameter of the metal cylinder. Since the diameter of the cone is constant, the height of the conical heap can also be used as direct measure of the flowability. Powders of very good flowability have a height of 15-20 mm for the conical heap; powders with a height of >50 mm for the conical heap have a poor flow behavior (table 2).

TABLE 2

Assessment of the flowability with height of the conical heap

| Height of conical heap [mm] | Assessment | Score |
|---|---|---|
| <20 | very good | 1 |
| 21-30 | good | 2 |
| 31-40 | just adequate | 3 |
| 41-50 | deficient | 4 |
| >50 | inadequate | 5 |

(c) Pressure Resistance

Powdered products tend to cake together on piling in sacks, drums or hoppers. The following test is used to assess their "piling stability": a steel cylinder with an internal diameter of 50 mm is filled to a height of about 20 mm with the powder to be tested, which is loaded with a plunger weighing 1.2 kg and with a defined additional weight. The duration of the exposure to pressure can be chosen appropriate for the particular stress on the powder during packaging, transport and storage. The additional weight used in this test design amounted to about 0.16-0.17 kg/cm$^2$, corresponding to the weight of 10 to 12 sacks of a given size, each with a filled weight of 50 kg, lying one on top of the other. After exposure to pressure for 24 hours, the additional weight was removed, the two cylinders were carefully rotated by 180° by hand, and the powder tablet was expelled from the casing with the aid of the plunger. The hardness of the powder tablet is regarded as a measure of the pressure resistance; it can be measured subjectively or with the aid of a drum sieve: for the measurement, the powder tablet was placed in a cylindrical drum sieve. The drum sieve was rotated at 60 rpm with the aid of a motor, and the time after which the tablet had only half the weight was determined. For this purpose, a balance which displayed the abraded powder weight was located underneath the sieve.

TABLE 3

Visual assessment of the pressure resistance

| Score | Behavior characteristics |
| --- | --- |
| 1 = very good | completely unchanged and flowing smoothly through orifice vessel No. 2 (table 1) |
| 2 = good | partly loosely adherent, easily disintegrating into the original state |
| 3 = quite good | loosely shaped; very substantially disintegrating to powder under gentle finger pressure |
| 4 = adequate | loosely caked; still disintegrating very finely with finger test |
| 5 = deficient | semisolid caking; no longer disintegrating very finely with finger test |
| 6 = inadequate | solidly shaped |

Test Results

Comparative examples 1 to 2 were carried out with compositions exclusively containing lipoic acid produced according to the prior art. (Example 1: according to EP 593 896; example 2: according to DE 199 38 621 A1)

Comparative examples 3 to 5 were carried out with compositions which contain lipoic acid produced according to the prior art of example 2 and non-inventive flow aids.

Examples 6 to 19 of the invention were carried out with compositions of the invention which contained lipoic acid produced according to example 2 and flow aids of the invention.

All lipoic acid compositions combined with flow aid were produced by mixing in a Turbula mixer for 3 minutes, followed by sieving through a 600 μm sieve.

The results in terms of the flow score are always considerably better in examples 6-19 than in example 2 (control).

Comparative example 5 serves as control for the height of the conical heap. The results in terms of this are likewise all better in examples 6-17.

The pressure resistance increases as a function of the concentration in the examples of the invention. With lipoic acid contents of 3.0% by weight, the increase in the scores is at least 1.5 in relation to example 2 (example 19: scores of 2.5 with 2.0% by weight).

TABLE 4

Results

| # | Flow aid | Proportion by weight | Flow score | Height of conical heap [mm] | Pressure resistance |
| --- | --- | --- | --- | --- | --- |
| 1 | n/a | n/a | 4 | 30 | 4-5 |
| 2 | n/a | n/a | 6 | not measurable, cone breaks off | 6 |
| 3 | Sipernat ® | 1.0 | 5 | not measurable, cone breaks off | 5-6 |
| 4 | 320 | 1.5 | 5 | | 5-6 |
| 5 | | 2.0 | 4 | 29 | 5 |
| 6 | Sipernat ® | 1.0 | 2 | 25 | 6 |
| 7 | 22S | 1.5 | 2 | 22 | 5-6 |
| 8 | | 2.0 | 2 | 21 | 5 |
| 9 | | 3.0 | 2 | 20 | 4-5 |
| 10 | Sipernat ® | 1.0 | 2 | 23 | 5 |
| 11 | 50S | 1.5 | 2 | 21 | 4-5 |
| 12 | | 2.0 | 2 | 19 | 4 |
| 13 | | 3.0 | 2 | 19 | 4 |
| 14 | Sipernat ® | 1.0 | 2 | 22 | 4-5 |
| 15 | 500LS | 1.5 | 2 | 19 | 4 |
| 16 | | 2.0 | 2 | 19 | 3-4 |
| 17 | | 3.0 | 2 | 20 | 3- |
| 18 | Silox ™ 2 | 1.5 | 4 | n/a | 4-5 |
| 19 | | 2.0 | 3 | n/a | 3-4 |

"n/a": not ascertainable

The invention claimed is:

1. A composition consisting of from 97.0 to 99.0 wt. %, based on the total weight of the composition, of a lipoic acid component and from 1.0 to 3.0 wt. %, based on the total weight of the composition, of a silica-based flow aid which has a particle size (×100 value) of from 50 to <600 μm and a tamped density of from 50 to 600 g/l, wherein the composition is free-flowing and powdery.

2. The composition as claimed in claim 1, wherein the lipoic acid component is racemic α-lipoic acid, dihydrolipoic acid, enantiopure R-(+)- or S-(−)-α-lipoic acid, enantiopure R-(+)- or S-(−)-α-dihydrolipoic acid or mixtures thereof.

3. The composition as claimed in claim 1, wherein at least a portion of the lipoic acid component is a salt.

4. The composition as claimed in claim 1, wherein the flow aid is present in an amount of from 2.0 to 3.0 wt. % based on the total weight of said composition.

5. The composition as claimed in claim 1, wherein the flow aid is selected from the group consisting of an hydrophilic spray-dried precipitated silica, an hydrophilic highly dispersed silica and an hydrophobic silica.

6. The composition as claimed in claim 1, wherein the flow aid is an amorphous silica gel.

7. The composition as claimed in claim 1, wherein the flow aid has a tamped density of from 75 to 100 g/l.

8. The composition as claimed in claim 1, wherein the flow aid has a specific surface area of from 30 to 1000 m$^2$/g.

9. The composition as claimed in claim 1, wherein the flow aid brings about a pH of from 3.0 to 11.5 in a concentration of 5% in aqueous solution.

10. A solid dosage form comprising the composition of claim 1 and a pharmaceutical adjuvant.

11. A solid dosage form as claimed in claim 10, in a compressed form.

12. A solution for infusion comprising the composition of claim 1 in a solution.

13. The composition of claim 3, wherein the salt is a sodium, potassium, ammonium, magnesium, or creatine lipoate.

14. The composition of claim 3, wherein the salt is a sodium, potassium, magnesium or creatine dihydrolipoate.

15. The composition of claim 3, wherein said salt is a salt of a basic amino acid.

16. The composition of claim 15, wherein said basic amino acid is lysine, arginine or ornithine.

17. The composition of claim 1, wherein said flow aid is present in an amount of from 1.5 to 3.0% by weight based on the total weight of said composition.

18. The composition as claimed in claim 8, wherein the specific surface area is from 190 to 450 $m^2/g$.

19. The composition of claim 9, wherein the flow aid brings about a pH of from 6.0 to 7.0 in a concentration of 5% in aqueous solution.

* * * * *